(12) United States Patent
Rao et al.

(10) Patent No.: US 6,274,780 B1
(45) Date of Patent: Aug. 14, 2001

(54) CATALYSTS FOR HALOGENATED HYDROCARBON PROCESSING AND THEIR PREPARATION AND USE

(75) Inventors: V. N. Mallikarjuna Rao, Wilmington, DE (US); Munirpallam A. Subramanian, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 533 days.

(21) Appl. No.: 08/677,062

(22) Filed: Jul. 9, 1996

Related U.S. Application Data

(60) Provisional application No. 60/001,066, filed on Jul. 11, 1995.

(51) Int. Cl.$^7$ .......................... C07C 17/00; C07C 19/08
(52) U.S. Cl. .................. 570/163; 502/228; 502/320; 570/164; 570/165; 570/166; 570/167; 570/168
(58) Field of Search .................................. 502/228, 320; 570/163–168

(56) References Cited

U.S. PATENT DOCUMENTS

| | | | |
|---|---|---|---|
| 2,744,148 | * 5/1956 | Ruh et al. | 260/653 |
| 3,787,331 | * 1/1974 | Gropelli et al. | 252/442 |
| 4,147,733 | * 4/1979 | Fiske et al. | 260/653.4 |
| 4,766,259 | * 8/1988 | Manzer et al. | 570/168 |
| 5,321,170 | * 6/1994 | Corbin et al. | 570/168 |
| 5,559,069 | * 9/1996 | Rao et al. | 502/226 |

FOREIGN PATENT DOCUMENTS

| | | | |
|---|---|---|---|
| WO 92/02476 | 2/1992 | (WO) | C07C/17/24 |
| WO 92/16479 | 10/1992 | (WO) | C07C/17/00 |

OTHER PUBLICATIONS

L.E. Manzer and V.N.M. Rao, Catalytic Synthesis of Chlorofluorocarbon Alternatives, *Advances in Catalysis*, 39, 329–350, 1993.

Karl Wieghardt, Hans Siebert, Schwingungsspektren under Kristallgitter von Hexamminchrom(III)–und Hexamminkobalt(III)–Hexafluorometallaten(III), *Journal of Molecular Structure*, 7, 305–313, 1971.

D.–H.Menz and B. Ehrhardt, Study of the Thermal Behaviour of [Cr(NH3)6]MF6(M=Cr,Al,Fe,Ga and In) and [Cr(NH3)6]F3 HF H20, *Journal of Thermal Analysis*, 42, 925–935, 1994.

\* cited by examiner

*Primary Examiner*—Marian C Knode
*Assistant Examiner*—Nadine Preisch

(57) ABSTRACT

A process is disclosed for changing the fluorine content of halogenated hydrocarbons containing from 1 to 6 carbon atoms, in the presence of a multiphase catalyst. The process involves producing the catalyst by heating a single phase solid catalyst precursor having the formula $(NH_3)_6Cr_{2-x}M_xF_6$ (where x is in the range of 0.1 to 1 and M is at least one metal selected from the group consisting of Al, Sc, V, Fe, Ga and In) to about 400° or less to produce a multiphase composition wherein a phase containing crystalline M fluoride is homogeneously dispersed with a phase containing chromium fluoride. Also disclosed are multiphase catalyst compositions consisting essentially of chromium fluoride and a crystalline fluoride of at least one metal selected from the above group (provided the atom percent of Cr is at least equal to the atom percent of the crystalline fluoride metals). Phases of the crystalline fluorides are homogeneously dispersed with phases of the chromium fluoride. Preparation of homogeneously dispersed multiphase catalyst compositions consisting essentially of fluorides of chromium and crystalline fluorides of at least one other metal selected from the above group (the atom percent Cr being at least equal to the atom percent of the other metal(s)) is also disclosed.

12 Claims, No Drawings

CATALYSTS FOR HALOGENATED HYDROCARBON PROCESSING AND THEIR PREPARATION AND USE

This application claims the priority benefit of U.S. Provisional Application No. 60/001,066, filed Jul. 11, 1995.

FIELD OF THE INVENTION

This invention relates to fluoride compositions, and their preparation and use, and more particularly to chromium and aluminum fluoride catalysts and preparation and use of such catalysts for processing halogenated hydrocarbons.

BACKGROUND

Numerous processes have been developed for changing the fluorine content of halogenated hydrocarbons using chromium containing catalysts. These include increasing the amount of fluorine of halogenated hydrocarbons which are not fully fluorinated, decreasing the fluorine content of halogenated hydrocarbons containing fluorine, and redistributing the number of fluorine atoms among two or more hydrocarbon molecules which are not fully fluorinated.

Various catalysts have been proposed for use in facilitating processes such as hydrofluorination, hydrochlorination (i.e., fluorine substitution by chlorine) and disproportionation which involve halogenated hydrocarbons. See, e.g., L. E. Manzer et al., Adv. Catal. 39, pp. 329–350 (1993). A well known class of art catalysts includes chromium supported on alumina, fluorinated alumina or aluminum fluoride. Typically these materials are prepared by depositing a soluble salt of chromium on an alumina or aluminum fluoride support. While this method does produce a combination catalyst, the support material and the material deposited thereon are not uniformly mixed. Techniques such as coprecipitation which rely upon physical characteristics of individual components (e.g., solubility) also typically yield non-homogeneously dispersed products due to differences in physical and chemical properties of the components. There is an interest in developing means for a more homogeneous dispersion of chromium on an aluminum fluoride support which can be used as a catalyst for changing the fluorine content of halogenated hydrocarbons.

SUMMARY OF THE INVENTION

This invention provides a process for changing the fluorine content of halogenated hydrocarbons containing from 1 to 6 carbon atoms, in the presence of a multiphase catalyst. The process is characterized by producing said catalyst by heating a single phase solid catalyst precursor having the formula $(NH_3)_6Cr_{2-x}M_xF_6$ where x is in the range of 0.1 to 1 and M is at least one metal selected from the group consisting of Al, Sc, V, Fe, Ga and In, to about 400° C. or less to produce a multiphase composition wherein a phase containing crystalline M fluoride is homogeneously dispersed with a phase containing chromium fluoride.

This invention also provides multiphase catalyst compositions consisting essentially of chromium fluoride and a crystalline fluoride of at least one metal selected from the group consisting of Al, Sc, V, Fe, Ga and In, provided the atom percent of Cr is at least equal to the atom percent of said crystalline fluoride metals, wherein phases of said crystalline fluorides are homogeneously dispersed with phases of said chromium fluoride. A homogeneously dispersed multiphase catalyst composition consisting essentially of fluorides of chromium and crystalline fluorides of at least one other metal selected from the group consisting of Al, Sc, V, Fe, Ga and In wherein the atom percent Cr is at least equal to the atom percent of said at least one other metal may be prepared in accordance with this invention by heating a corresponding single phase solid catalyst precursor composition of the formula $(NH_3)_6Cr_{2-x}M_xF_6$ wherein M and x are as defined above, to a temperature sufficient to remove essentially all the nitrogen-containing component of said formula composition to produce a multiphase composition wherein a phase containing crystalline M fluoride is homogeneously dispersed with a phase containing chromium fluoride.

DETAILED DESCRIPTION

The catalytic process of this invention for changing the fluorine content of halogenated hydrocarbons containing from 1 to 6 carbon atoms employs a multiphase catalyst prepared in a manner which provided homogeneous dispersion of multiple metal components by converting a decomposable single phase solid catalyst precursor to a multiple phase catalyst. A single phase catalyst precursor of the formula $(NH_3)_6Cr_{2-x}M_xF_6$ may be prepared by conventional synthetic techniques (e.g., crystallization). Normally, the ratio of the metal components, (2−x):(x), should be between 19:1 and 1:1. Of particular note are compositions where the ratio of Cr to M (e.g., Al) in the precursors is about 1:1 (i.e., x is about 1).

It will be evident that providing single phase precursors as described arranges the two components, Cr and M, in a structured arrangement where Cr and M are closely connected through the $NH_3$ and F components. As a result of the arrangement of the components in the precursor, when the single phase structure collapses upon heating, uniformly interspersed phases of Cr and M are formed. These are referred to herein as "homogeneously dispersed" phases.

It is desirable to convert the single phase precursor to multiphase composition at a moderately elevated temperature (e.g., about 400° C. or less). While some single phase structures are unstable and collapse upon heating, this conversion is ordinarily accomplished by decomposing the decomposable nitrogen-containing component of the composition. Accordingly, the decomposable nitrogen-containing component preferably decomposes at about 400° C. or less.

The catalysts used for changing the fluorine content of halogenated hydrocarbons should contain fluoride. When the multiphase composition is produced by heating the single phase precursor in air or other oxygen-containing atmosphere (e.g., $O_2$) oxyfluorides and/or oxides may be present. These may be at least partially converted to fluoride by contacting the multiphase composition with a vaporizable fluorine-containing fluorinating compound. Typically, where additional fluoride is desired, a multiphase composition is treated with a vaporizable fluorine-containing fluorinating compound such as HF, $SF_4$, $COF_2$, $CCl_3F$, $CCl_2F_2$, $CHF_3$ or $CCl_2FCClF_2$, at elevated temperatures (e.g., at about 200° C. to about 450° C.) until the desired degree of fluorination is obtained (see, e.g., U.S. Pat. No. 4,902,838).

Included in this invention is a process for increasing the fluorine content of a saturated or olefinic compound having the formula $C_nH_aF_bX_c$, wherein n is 1 to 6, a is 0 to 12, b is 0 to 13 and c is 1 to 13, and where each X is independently selected from Cl and Br, by reacting the saturated compounds with HF in the vapor phase. The present invention also provides a process for the disproportionation of a compound having the formula $C_pH_gF_hCl_j$, where p is an integer from 1 to 2, g is an integer from 0 to 3, h is an integer from 1 to 4 and j is an integer from 1 to 3. These processes are respectively characterized by reacting the $C_nH_aF_bX_c$ compound with HF and conducting the disproportionation of the $C_pH_gF_hCl$ compound, in the presence of a mutiphase catalyst containing fluorine, which has a phase containing chromium fluoride homogeneously dispersed with a phase containing a fluoride of a metal selected from the group consisting of Al, Sc, V, Fe, Ga, In and mixtures thereof. The mutiphase catalyst containing fluorine can be prepared by heating a corresponding single phase fluoride composition of the formula $(NH_3)_6Cr_{2-x}M_xF_6$ wherein M and x are as defined above, to a temperature sufficient to remove all the nitrogen-containing component of the composition. A more active catalyst may often be achieved by contacting the multiphase composition with a vaporizable fluorine-containing fluorinating compound. Typically, the multiphase composition can be treated with a vaporizable fluorine-containing fluorinating compound such as HF, $SF_4$, $COF_2$, $CCl_3F$, $CCl_2F_2$, $CHF_3$ or $CCl_2FCClF_2$, at elevated temperatures (e.g., at about 200° C. to about 450° C.). Nevertheless this treatment is not essential.

In one embodiment a homogeneously dispersed multiphase composition consisting of chromium fluoride and beta-$AlF_3$ is prepared from $(NH_3)_6CrAlF_6$ a known compound (K. Wieghardt et al., J. Mol. Struc., 7, 305–313 (1971)) by heating at about 350° C. to about 400° C. for a suitable period (typically one hour or more), preferably in air. Essentially all the nitrogen-containing component will be decomposed.

The reaction of said compounds of the formula $C_nH_aF_bX_c$ with HF in the presence of the catalyst of the instant invention is conducted at about 150° C. to 500° C., preferably for saturated compounds at about 175° C. to 400° C., and more preferably for saturated compounds at about 200° C. to about 350° C., with a contact time of about 1 to about 120 seconds, preferably about 5 to about 60 seconds. The amount of HF should be at least a stoichiometric amount. Typically, the molar ratio of HF to the said compounds of the formula $C_nH_aF_bX_c$ can range from about 1:1 to about 100:1, preferably about 2:1 to 50:1, and more preferably about 3:1 to 10:1. In general, with a given catalyst composition, the higher the temperature and the longer the contact time, the greater is the conversion to fluorinated products. The above variables can be balanced, one against the other, so that the formation of higher fluorine substituted products is maximized.

Examples of olefinic compounds which may be reacted with HF include $CHCl=CCl_2$, $CCl_2=CCl_2$, $CCl_3CCl=CClCCl_3$, $CH_2=CCl_2$, $CCl_2=CClCCl_3$, $CHF=CF_2$, $CH_2=CF_2$ and $CClF=CF_2$. Of note is a catalytic process for producing 2-chloro-1,1,1-trifluoroethane (HCFC-133a) by the fluorination of a trihaloethene of the formula $CX_2=CHCl$ wherein each X is chlorine or fluorine. Starting materials include trichloroethene, 1,2-dichlorofluoroethene and 1-chloro-2,2-difluoroethene. Trichloroethene is preferred. HCFC-133a is produced by reacting the above unsaturated compounds with HF in the vapor phase in the presence of the catalyst of this invention. The reaction of the above trihaloethenes with HF in the presence of the catalyst of the instant invention is conducted at about 150° C. to 350° C., more preferably about 175° C. to 250° C. Oxygen may be added, if desired.

Also of note is a catalytic process for producing 2,2-dichloro-1,1,1-trifluoroethane ($CHCl_2CF_3$, i.e., HCFC-123), 1,1,1,2-tetrafluorochloroethane ($CHClFCF_3$, i.e., HCFC-124) and pentafluoroethane ($CHF_2CF_3$, i.e., HFC-125) by the fluorination of a tetrahaloethene of the formula $C_2Cl_{4-y}F_y$, wherein y equals 0 to 3. Starting materials include $CCl_2=CCl_2$, $CClF=CCl_2$, $CClF=CClF$ $CF_2=CCl_2$, and $CF_2=CClF$. Tetrachloroethene is preferred. HCFC-123, HCFC-124 and/or HFC-125 is produced by reacting the above unsaturated compounds with HF in the vapor phase in the presence of the catalyst of this invention.

Examples of saturated compounds which may be reacted with HF include $CH_2Cl_2$, $CHCl_3$, $C_2Cl_6$, $C_2H_4Cl_2$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$ and $CCl_3CH_2CCl_3$. Of note are catalytic processes for reacting 1,1,1-trichloro-1,1,1-trifluoroethane ($CCl_3CF_3$, i.e., CFC-113a), or reacting dichloromethane, with HF, in the vapor phase in the presence of the catalyst of this invention. For the reaction of CFC-113a with HF to yield $CCl_2FCF_3$ (CFC-114a), the HF:$CCl_3CF_3$ ratio can vary widely. The HF:113a ratio should be at least stoichiometric but preferably can vary from about 2:1 to about 10:1.

For the reaction of dichloromethane to yield difluoromethane ($CH_2F_2$, HFC-32), the molar ratio of HF to $CH_2Cl_2$ preferred ranges from about 1:1 to about 10:1. The reaction temperature normally ranges from about 180° C. to about 375° C. (e.g., from about 200° C. to about 350° C.)

The homogeneously dispersed chromium fluoride and beta aluminum fluoride catalyst may be used in accordance with this invention in a catalytic process for the disproportionation of hydrochlorofluorocarbons of the formula, $C_pH_gF_hCl_j$ having from 1 to 2 carbon atoms, at least one hydrogen and at least one fluorine, to produce hydrofluorocarbons.

Suitable halofluorocarbons for disproportionation include $CH_2ClF$, $CH_3CClF_2$, $CCl_2FCClF_2$ and $CHClFCF_3$. The products of the disproportionation reactions are respectively, $CH_2F_2$ and $CH_2Cl_2$, $CH_3CF_3$ and $CH_2=CCl_2$, $C_2Cl_4F_2$ and $C_2Cl_2F_4$, and $CHCl_2CF_3$ and $CHF_2CF_3$. In certain embodiments substantial isomerization can occur.

Reactions for changing the fluorine content of a halogenated hydrocarbon (e.g., the reaction of compounds of the formula $C_nH_aF_bX_c$ with HF and the disproportionation of compounds of the formula $C_pH_gF_hCl_j$) may be conducted in any suitable reactor, including fixed and fluidized bed reactors. The reaction vessel should be constructed from materials which are resistant to the corrosive effects of hydrogen fluoride and hydrogen chloride such as Inconel™ nickel alloy and Hastelloy™ nickel alloy.

The reaction products may be separated by conventional techniques, such as distillation. It is noted that many halogenated hydrocarbon products of the above reactions form azeotropes with HF, HCl or other halogenated hydrocarbons.

Some of the reaction products will have desired properties for commercial use. For example $CCl_3CF_3$ (CFC-113a) can be used to prepare CFC-114a which can then be converted to $CH_2FCF_3$ (HFC-134a) by hydro-dechlorination. Others, such as $CCl_2=CCl_2$ can be recycled back to reactors which are being used for the synthesis of halofluorocarbons.

Pressure is not critical. Atmospheric and super-atmospheric pressures are the most convenient and are therefore preferred.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

Catalyst Preparation

Catalyst A $(NH_3)_6CrCl_6$ (8.3565 g, >95% purity) and $AlCl_3 \cdot 6H_2O$ (7.2429 g, 99% pure) were dissolved separately in deionized water (50 mL). The solutions were mixed together in a Teflon® container. To the mixture was added 48% aqueous HF (25 mL) and the mixture was heated to 110° C. for 2 hours with stirring. The light green precipitate which formed was filtered, washed with deionized water, and dried at 105° C. for 12 hours. The x-ray diffraction pattern of the product ($(NH_3)_6CrAlF_6$) showed it was essentially a single phase. The x-ray pattern could be indexed on the basis of cubic unit cell parameter (a=9.974, space group: Pa3). [Wieghardt and Siebert, J. Mol. Struc. 7, 305 (1971)].

$(NH_3)_6CrAlF_6$ was heated to 375° C. for 12 hours in air, and the x-ray pattern of the resulting brown product essentially showed the presence of beta-$AlF_3$ and an amorphous phase. Microprobe analysis showed the presence of Al, Cr and F in an atomic ratio of about 1:1:6. The product was granulated to form 1.3 to 1.7 mm size particles for catalytic tests.

Catalyst B $CrF_3 \cdot 4H_2O$ (18.1 g, 98% purity) and anhydrous $AlF_3$ (8.4 g, 99+% pure) were mixed thoroughly for 1 hour in an automatic agate mortar and the resulting powder was heated to 375° C. for 12 hours in an alumina tray. The x-ray diffraction pattern of the resulting brown product showed the presence of alpha-$AlF_3$ and poorly crystallized $Cr_2O_3$. The product was granulated to form 1.3 to 1.7 mm size particles for catalytic tests.

Catalyst C

Anhydrous $CrF_3$ (10.9 g) and anhydrous $AlF_3$ (8.4 g, 99+% pure) were mixed thoroughly for 1 hour in an automatic agate mortar and the resulting powder was heated to 375° C. for 12 hours in an alumina tray. The x-ray diffraction pattern of the brown product showed the presence of alfa-$AlF_3$ (50%), $Cr_2O_3$ (40%) and $CrOF2$ (10%). The product was granulated to form 1.3 to 1.7 mm size particles for catalytic tests.

Catalyst D

Anhydrous $CrF_3$ (10.9 g) and $AlF_3 \cdot 3H_2O$ (13.8 g) were mixed thoroughly for 1 hour in an automatic agate mortar and the resulting powder was heated to 375° C. for 12 hours in an alumina tray. The x-ray diffraction pattern of the brown product showed the presence of alfa-$AlF_3$ and amorphous phase. The product was granulated to form 1.3 to 1.7 mm size particles for catalytic tests.

General Procedure for Catalyst Evaluation

The evaluation of catalysts was carried out in a fixed-bed reactor maintained in a fluidized sandbath. It consisted of a 12" (30.5 cm)×¾" (1.9 cm) Inconel™ nickel alloy pipe having an internal diameter of 16 mm. A ⅛" (0.32 cm) thermowell extended through the length of the reactor, allowing for temperature measurement at specific points. Usually the temperature was measured at the center of the bed. The feed materials were sent downflow through the reactor. The reactor was charged with the catalyst to be evaluated. It was then heated to about 250° C. in a flow of nitrogen (50 cc/min) for about 30 minutes. The temperature was reduced to 175° C. and an HF:nitrogen flow in the ratio of 1:1 (total flow 100 cc/min) was passed through. After HF was observed in the reactor exit, the HF/nitrogen flow was changed to a 4:1 ratio and the temperature of the reactor gradually increased to 400° C. The reactor and contents were kept at 400° C. for about 30 minutes. The reactor and contents were then brought to the desired operating conditions for evaluation of catalysts.

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×⅛" (0.32 cm) diameter tube containing Krytox™ perfluorinated polyether on an inert carbon support. The helium flow was 35 cc/min. Gas chromatographic conditions were 70° C. for an initial hold period of three minutes followed by temperature programming to 180° C. at a rate of 6° C./minute. Unless otherwise indicated, the reported results are in mole %.

The bulk of the reactor effluent containing organic products and also inorganic acids such as HCl and HF was treated with aqueous caustic to neutralize the acids prior to disposal.

| Legend | |
|---|---|
| F115 is $CF_3CF_2Cl$ | F32 is $CH_2F_2$ |
| F114 is $CF_2ClCF_2Cl$ | F31 is $CH_2FCl$ |
| F114a is $CF_3CFCl_2$ | F152a is $CH_3CHF_2$ |
| F113 is $CF_2ClCFCl_2$ | F152 is $CH_2FCH_2F$ |
| F113a is $CF_3CCl_3$ | F151 is $CH_2ClCH_2F$ |
| F112 is $CFCl_2CFCl_2$ | F151a is $CH_3CHClF$ |
| F112a is $CF_2ClCCl_3$ | F150a is $CH_3CHCl_2$ |
| F125 is $CF_3CHF_2$ | F150 is $CH_2ClCH_2Cl$ |
| F124 is $CF_3CFHCl$ | F1112a is $CF_2{=}CCl_2$ |
| F124a is $CF_2ClCF_2H$ | F1122 is $CFCl{=}CHF$ |
| F123 is $CF_3CHCl_2$ | F1141 is $CH_2{=}CHF$ |
| F134a is $CF_3CH_2F$ | F1140 is $CH_2{=}CHCl$ |
| F133a is $CF_3CH_2Cl$ | PCE is $CCl_2{=}CCl_2$ |

Example 1

Catalyst A (16.0 g, 20 mL)

Fluorination of 113a

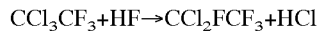

The feed material to the reactor analyzed as 98.9% F113a, and 0.8% F113. The HF to organic ratio was 2:1. Temperature (Temp, degrees Celsius) and contact times (C.T., seconds) were varied. The results are shown in the table.

| Hrs. | Temp | C.T. | F115 | F114a | F113a |
|---|---|---|---|---|---|
| 0.5 | 275 | 15 | 0.1 | 62.9 | 37.0 |
| 1.5 | 275 | 15 | 0.1 | 58.9 | 41.1 |
| 2.0 | 275 | 30 | 0.1 | 76.4 | 23.5 |
| 3.5 | 275 | 30 | 0.1 | 75.4 | 24.5 |
| 4.0 | 300 | 30 | 1.0 | 93.5 | 5.4 |

-continued

| Hrs. | Temp | C.T. | F115 | F114a | F113a |
|---|---|---|---|---|---|
| 4.5 | 300 | 30 | 1.1 | 93.5 | 5.3 |
| 5.0 | 300 | 15 | 0.8 | 93.2 | 6.0 |
| 5.5 | 300 | 15 | 0.9 | 93.0 | 6.1 |
| 6.0 | 300 | 5 | 0.3 | 84.0 | 15.6 |
| 6.5 | 300 | 5 | 0.4 | 87.2 | 12.4 |

Example 2

Catalyst A (16.0 g, 20 mL)

Fluorination of Dichloromethane

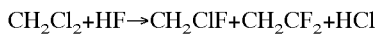
$CH_2Cl_2 + HF \rightarrow CH_2ClF + CH_2CF_2 + HCl$

The fluorination of dichloromethane was carried out at 225° C. with an HF to organic ratio of 4:1 and a contact time of 15 seconds. The results are shown in the table below.

| Hrs. | F32 | F31 | $CH_2Cl_2$ |
|---|---|---|---|
| 0.5 | 46.9 | 12.0 | 41.0 |
| 2.5 | 52.3 | 11.8 | 35.8 |
| 3.5 | 50.4 | 11.9 | 37.5 |
| 4.5 | 53.6 | 11.7 | 34.6 |
| 5.5 | 62.8 | 11.1 | 26.1 |
| 6.5 | 57.5 | 11.5 | 30.9 |
| 7.5 | 54.1 | 11.7 | 34.1 |
| 8.5 | 52.9 | 11.8 | 35.2 |

Comparative Example A

Catalyst B (13.5 g, 17 mL)

Fluorination of Dichloromethane

$CH_2Cl_2 + HF \rightarrow CH_2ClF + CH_2CF_2 + HCl$

The HF to dichloromethane mole ratio was 4:1 and the contact time was 15 seconds. The results at various temperatures are shown in the table below.

| Hrs. | Temp. | F32 | F31 | $CH_2Cl_2$ |
|---|---|---|---|---|
| 0.5 | 200 | 7.0 | 16.0 | 76.8 |
| 1.0 | 200 | 6.6 | 16.3 | 76.7 |
| 1.5 | 200 | 6.0 | 15.9 | 77.8 |
| 2.0 | 225 | 35.3 | 14.8 | 49.4 |
| 2.5 | 225 | 35.9 | 14.7 | 49.0 |
| 3.0 | 225 | 34.8 | 14.9 | 49.8 |
| 3.5 | 225 | 29.2 | 15.9 | 54.5 |

Comparative Example B

Catalyst C (16.0 g, 17 mL)

Fluorination of Dichloromethane

$CH_2Cl_2 + HF \rightarrow CH_2ClF + CH_2CF_2 + HCl$

The HF to organic molar ratio was 4:1 and the contact time was 15 seconds. The results at various temperatures are shown in the table below.

| Hrs. | Temp. | F32 | F31 | $CH_2Cl_2$ |
|---|---|---|---|---|
| 0.5 | 200 | 11.0 | 16.6 | 72.3 |
| 1.5 | 200 | 8.8 | 16.3 | 74.6 |
| 2.5 | 200 | 6.2 | 14.9 | 78.6 |
| 3.0 | 225 | 42.1 | 13.9 | 43.8 |
| 4.5 | 225 | 31.7 | 15.5 | 52.3 |
| 5.5 | 225 | 26.8 | 15.1 | 57.8 |
| 7.0 | 225 | 20.9 | 17.2 | 61.5 |

Comparative Example C

Catalyst D (10.8 g, 13 mL)

Fluorination of Dichloromethane $CH_2Cl_2 + HF \rightarrow CH_2ClF + CH_2CF_2 + HCl$ The HF to organic molar ratio was 4:1 and the contact time was 15 seconds. The results at various temperatures are shown in the table below.

| Hrs | Temp | F32 | F31 | $CH_2Cl_2$ |
|---|---|---|---|---|
| 1.5 | 225 | 42.5 | 12.0 | 45.3 |
| 2.5 | 225 | 57.5 | 11.4 | 31.0 |
| 3.0 | 225 | 64.4 | 10.8 | 24.6 |
| 5.0 | 225 | 51.1 | 11.8 | 37.0 |
| 7.0 | 225 | 63.3 | 10.9 | 25.6 |
| 9.0 | 225 | 57.7 | 11.4 | 30.7 |
| 11.0 | 225 | 58.2 | 11.4 | 30.2 |
| 13.0 | 225 | 53.7 | 11.7 | 34.5 |
| 15.0 | 225 | 62.8 | 11.0 | 26.0 |
| 17.0 | 225 | 57.6 | 11.4 | 30.8 |
| 19.0 | 225 | 53.0 | 11.7 | 35.1 |
| 21.0 | 200 | 48.9 | 10.9 | 40.1 |
| 22.0 | 200 | 63.8 | 9.9 | 26.2 |
| 23.0 | 175 | 19.6 | 12.2 | 68.1 |
| 23.5 | 175 | 17.3 | 12.4 | 70.2 |
| 24.0 | 175 | 18.8 | 12.4 | 68.6 |

Example 3

Catalyst A (16.0 g, 20 mL)

Fluorination of F124

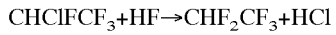
$CHClFCF_3 + HF \rightarrow CHF_2CF_3 + HCl$

The fluorination of F124 was carried out at a constant contact time of 15 seconds and an HF to organic molar ratio of 4:1 at various temperatures. The feed material to the reactor contained 99.8% F124. The results at various temperatures are shown in the table below.

| Temp. | F125 | F124 | F123 |
|---|---|---|---|
| 275 | 1.2 | 98.7 | |
| 300 | 5.8 | 93.7 | 0.2 |
| 325 | 38.2 | 56.6 | 5.0 |
| 350 | 67.9 | 24.6 | 7.1 |

Comparative Example D

Catalyst C (16.0 g, 17 mL)

Fluorination of F124

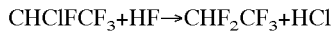
$CHClFCF_3 + HF \rightarrow CHF_2CF_3 + HCl$

The HF to molar organic ratio was 4:1 and the contact time was 15 seconds. The feed material analyzed for 99.8%

F124. The results at various temperatures are shown in the table below.

| Hrs. | Temp. | F125 | F124 |
|---|---|---|---|
| 0.5 | 275 | 0.4 | 99.4 |
| 1.0 | 275 | 0.4 | 99.4 |
| 1.5 | 300 | 2.6 | 97.0 |
| 2.0 | 325 | 10.9 | 87.6 |
| 2.5 | 350 | 33.9 | 60.2 |
| 3.0 | 350 | 35.8 | 57.9 |

Example 4

Catalyst A (16.0 g, 20 mL)

Fluorination of Perchloroethylene

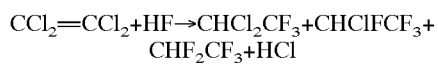
$CCl_2=CCl_2+HF \rightarrow CHCl_2CF_3+CHClFCF_3+CHF_2CF_3+HCl$

The fluorination of perchloroethylene was carried out at an HF to organic molar ratio of 6:1 at two different contact times and temperatures for a period of about 50 hours. The major products observed were as as shown in the table below.

| Temp. | C. T. | F125 | F124 | F123 | PCE |
|---|---|---|---|---|---|
| 325 | 30 | 21.3 | 22.0 | 25.7 | 21.7 |
| 325 | 15 | 11.6 | 21.9 | 26.0 | 30.4 |
| 350 | 30 | 43.5 | 16.0 | 18.0 | 12.1 |
| 350 | 15 | 27.0 | 18.6 | 19.9 | 24.0 |

Example 5

Catalyst A (16.0 g, 20 mL)

Fluorination of F133a

$CH_2ClCF_3+HF \rightarrow CH_2FCF_3$

The fluorination of F133a was carried out at a constant contact time of 10 seconds and an HF to organic molar ratio of 10:1. The feed material consisted of 99.1% F133a and 0.8% F114a. Product analysis is shown in the following table.

| Temp. | F143a | F125 | F134a | F1122 | F133a |
|---|---|---|---|---|---|
| 300 |  |  | 3.9 |  | 95.0 |
| 330 |  |  | 20.2 | 0.1 | 78.3 |
| 350 |  | 0.1 | 29.1 | 0.2 | 69.5 |
| 370 | 0.1 | 0.2 | 31.8 | 0.3 | 66.3 |
| 390 | 0.2 | 0.6 | 33.1 | 0.7 | 63.9 |

Example 6

Catalyst A (16.0 g, 20 mL)

Disproportionation of F124

$2CHClFCF_3 \rightarrow CHCl_2CF_3+CHF_2CF_3$

The disproportionation of F124 was carried out at a contact time of 60 seconds at various temperatures. The feed material to the reactor was 99.8% F124 and 0.2% F124a. The results are shown in the table below.

| Temp. | F125 | F124 | F123 |
|---|---|---|---|
| 150 | 9.1 | 82.4 | 8.3 |
| 175 | 13.3 | 74.4 | 12.2 |
| 200 | 35.3 | 30.7 | 33.8 |
| 225 | 42.5 | 17.2 | 39.6 |

Example 7

Catalyst A (16.0 g, 20 mL)

Isomerization of F113

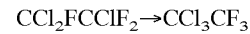
$CCl_2FCClF_2 \rightarrow CCl_3CF_3$

The isomerization of F113 was carried out at a constant contact time of 30 seconds at various temperatures. The feed material to the reactor contained 99.6% F113 and 0.3% F113a. The results are shown in the table below.

| Temp. | 115 | 114 | 114a | 113 | 113a | 1112a | 112 | 112a | PCE |
|---|---|---|---|---|---|---|---|---|---|
| 150 | 0.1 | 28.8 | 2.1 | 41.5 | 1.9 | 1.2 | 0.8 | 23.2 | 0.3 |
| 200 | 1.2 | 32.8 | 7.4 | 11.4 | 18.6 | 5.8 | 1.1 | 19.2 | 2.5 |
| 275 | 8.5 | 7.0 | 14.6 | 4.4 | 45.9 | 3.0 | 1.3 | 9.6 | 5.8 |
| 300 | 13.9 | 2.4 | 14.4 | 2.8 | 50.8 | 2.4 | 2.5 | 4.0 | 6.3 |

Example 8

Catalyst A (16.0 g, 20 mL)

Fluorination of 1,2-dichloroethane

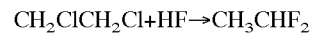
$CH_2ClCH_2Cl+HF \rightarrow CH_3CHF_2$

The starting 1,2-dichloroethane (F150) had a purity of 99.9%. The operating temperature was 225° C. The HF:150 molar ratios for the 15 second contact time runs was 4:1 and was 8:1 for the 30 second contact time runs. The reported results are in area % and are shown in the table below.

| C.T. | F1141 | F152a | F1140 | F151a | F151 | F150 |
|---|---|---|---|---|---|---|
| 15 | 0.5 | 14.7 | 4.4 | 0.2 | 7.3 | 72.6 |
| 30 | 0.8 | 32.8 | 5.2 | 0.5 | 5.5 | 55.1 |

Example 9

Catalyst A (16.0 g, 20 mL)

Fluorination of 1,1-dichloroethane

$$CH_3CHCl_2 + HF \rightarrow CH_3CHF_2$$

The starting 1,1-dichloroethane (F150a) had a purity of 99.6%. The HF to organic molar ratio was 4:1. The results are reported in area % and are shown in the table below.

| Temp. | C.T. | F1141 | F152a | F1140 | F151a | F150a |
|---|---|---|---|---|---|---|
| 200 | 30 | 8.8 | 64.6 | 23.5 | 1.0 | 0.1 |
| 200 | 30 | 6.2 | 68.2 | 22.3 | 1.4 | 0.2 |
| 200 | 30 | 4.5 | 60.8 | 31.1 | 1.8 | 0.5 |
| 150 | 15 | 4.4 | 27.1 | 59.0 | 6.6 | 2.2 |
| 150 | 15 | 1.9 | 16.5 | 45.1 | 16.6 | 19.7 |
| 150 | 15 | 1.2 | 12.3 | 35.0 | 18.3 | 33.0 |
| 150 | 15 | 1.0 | 10.5 | 29.6 | 18.6 | 40.3 |
| 175 | 15 | 0.6 | 24.8 | 34.0 | 14.0 | 26.6 |
| 175 | 15 | 0.5 | 22.5 | 32.5 | 14.5 | 29.9 |
| 175 | 15 | 0.4 | 20.0 | 31.1 | 14.7 | 33.8 |
| 200 | 15 | 0.7 | 49.3 | 40.2 | 5.1 | 4.6 |
| 200 | 15 | 0.7 | 49.8 | 39.9 | 5.0 | 4.5 |

There were small quantities of other products.

A comparison of Examples 8 and 9 indicate that less olefinic by-products are obtained from the reaction of 1,2-dichloroethane than from the reaction of 1,1-dichloroethane.

What is claimed is:

1. A method of preparing a homogeneously dispersed multiphase catalyst composition consisting essentially of fluorides of chromium and at least one other metal selected from the group consisting of Al, Sc, V, Fe, Ga and In wherein the atom percent of Cr is at least equal to the atom percent of said at least one other metal, characterized by: heating a single phase solid catalyst precursor composition of the formula $(NH_3)_6Cr_{2-x}M_xF_6$ where M is at least one metal selected from the group consisting of Al, Sc, V, Fe, Ga and In and x is in the range of 0.1 to 1 to a temperature sufficient to remove essentially all of the nitrogen-containing component of said formula composition to produce a multiphase composition wherein a phase containing crystalline M fluoride is homogeneously dispersed with a phase containing chromium fluoride.

2. A multiphase catalyst composition prepared in accordance with the process of claim 1.

3. A multiphase catalyst composition consisting essentially of chromium fluoride and a crystalline fluoride of at least one metal selected from the group consisting of Al, Sc, V, Fe, Ga and In, provided that the atom percent of Cr is at least equal to the atom percent of said crystalline fluoride metals, wherein phases of said crystalline fluorides are homogeneously dispersed with phases of said chromium fluoride.

4. A process for increasing the fluorine content of a saturated or olefinic compound having the formula $C_nH_aF_bX_c$ where n is an integer from 1 to 6, a is an integer from 0 to 12, b is an integer from 0 to 13, c is an integer from 1 to 13, and each X is independently selected from Cl and Br, in the presence of a multiphase catalyst, characterized by:

producing said catalyst by heating a single phase solid catalyst precursor having the formula $(NH_3)_6Cr_{2-x}M_xF_6$ wherein x is in the range of 0.1 to 1 and M is at least one metal element selected from the group consisting of Al, SC, V, Fe, Ga and In, to about 400° C. or less to produce a multiphase composition wherein a phase containing crystalline M fluoride is homogeneously dispersed with a phase containing chromium fluoride; and reacting said saturated or olefinic compound with HF in the vapor phase in the presence of said catalyst.

5. The process of claim 4 wherein M is Al and x is about 1.

6. The method of claim 1 wherein the nitrogen-containing compound of the single phase solid catalyst precursor decomposes at about 400° C. or less; and wherein the single phase solid catalyst precursor is heated to about 400° C. or less to produce the multiphase composition.

7. The method of claim 6 wherein the single phase solid catalyst precursor is $(NH_3)_6CrAlF_6$.

8. A multiphase catalyst composition prepared in accordance with the method of claim 6.

9. The multiphase catalyst composition of claim 3 consisting essentially of chromium fluoride and a crystalline fluoride of Al.

10. A process for increasing the fluorine content of a saturated or olefinic compound having the formula $C_nH_aF_bX_c$ where n is an integer from 1 to 6, a is an integer from 0 to 12, b is an integer from 0 to 13, c is an integer from 1 to 13, and each X is independently selected from Cl and Br, in the presence of a multiphase catalyst, characterized by:

reacting said saturated or olefinic compound with HF in the vapor phase in the presence of the multiphase catalyst composition of claim 2, claim 3, claim 8, or claim 9.

11. A process for changing the fluorine content of a halogenated hydrocarbon compound having the formula $C_pH_gF_hCl_j$ where p is an integer from 1 to 2, g is an integer from 1 to 3, h is an integer from 1 to 4, and j is an integer from 1 to 3, in the presence of a multiphase catalyst, characterized by:

conducting a disproportionation of said compound in the presence of the multiphase catalyst composition of claim 2, claim 3, claim 8 or claim 9.

12. A process for increasing the fluorine content of a saturated or olefinic compound having the formula $C_nH_aF_bX_c$ where n is an integer from 1 to 6, a is an integer from 0 to 12, b is an integer from 0 to 13, c is an integer from 1 to 13, and each X is independently selected from Cl and Br, in the presence of a multiphase catalyst, characterized by:

producing said multiphase catalyst by the method of claim 1, claim 6 or claim 7; and reacting said saturated or olefinic compound with HF in the vapor phase in the presence of the catalyst produced by said method.

* * * * *